United States Patent
Schueler et al.

(12) 
(10) Patent No.: US 6,468,778 B1
(45) Date of Patent: Oct. 22, 2002

(54) PROCESS FOR THE INACTIVATION OF VIRUSES

(75) Inventors: Eckhard Schueler, Marburg; Gerhardt Kumpe, Wetter; Thomas Nowak, Staufenberg, all of (DE)

(73) Assignee: Aventis Behring GmbH, Marburg (DE)

( * ) Notice: Subject to any disclaimer, the term of this patent is extended or adjusted under 35 U.S.C. 154(b) by 0 days.

(21) Appl. No.: 09/572,471

(22) Filed: May 17, 2000

(30) Foreign Application Priority Data

May 19, 1999 (DE) .......................................... 199 23 027

(51) Int. Cl.[7] .................................................. C12N 7/04
(52) U.S. Cl. ........................ 435/236; 435/2; 435/235.1; 435/238; 435/239; 422/1
(58) Field of Search ............................ 435/2, 236, 238, 435/239, 235.1; 422/1

(56) References Cited

U.S. PATENT DOCUMENTS

| | | |
|---|---|---|
| 4,687,664 A | 8/1987 | Philapitsch et al. |
| 4,749,783 A | 6/1988 | Jordan et al. |
| 5,593,675 A * | 1/1997 | Hodler et al. |
| 5,610,147 A | 3/1997 | Seelich |
| 5,770,199 A * | 6/1998 | Eibl et al. |
| 5,866,122 A * | 2/1999 | Turecek et al. |

FOREIGN PATENT DOCUMENTS

| | | |
|---|---|---|
| EP | 0 124 506 A2 | 11/1984 |
| EP | 0 124506 | 11/1984 |
| EP | 0 683 678 | 11/1995 |

OTHER PUBLICATIONS

European Search Report dated May 9, 2000.
English Language Abstract of EP 0 124 506.
English Language Abstract of EP 0 683 678.

* cited by examiner

Primary Examiner—Leon B. Lankford, Jr.
(74) Attorney, Agent, or Firm—Finnegan, Henderson, Farabow, Garrett & Dunner, L.L.P.

(57) ABSTRACT

A process for the inactivation and/or elimination of coated and/or noncoated viruses from a plasma protein solution by addition of an ammonium salt at alkaline pHs is described, in which a chromatographically prepurified plasma protein solution is subjected to an incubation at room temperature and at an ammonium salt concentration of 13 to 22% by weight, pasteurized at approximately 60° C. for several hours after separation of the precipitates and removal of the ammonium salt down to a residual content of less than 0.5 mol/l and then processed to give a therapeutically employable plasma protein preparation.

9 Claims, No Drawings

PROCESS FOR THE INACTIVATION OF VIRUSES

The invention relates to a process for the inactivation and/or elimination of coated and/or noncoated viruses from a plasma protein solution.

As is known, human plasma is a raw material for a number of modern therapeutics. These include albumin, the immunoglobulins and the group of blood clotting factors.

The need for blood clotting factors results from the necessity that patients with congenital deficiencies of individual clotting factors can only survive by substitution of these factors. In addition, however, there are also acquired deficiencies of blood clotting factors, which likewise make substitution necessary.

Although it was initially assumed that the substitution of plasma proteins is without risk for the patient, it soon emerged that as a result of therapy with preparations of this type infectious diseases can be transmitted from the plasma donor, which in many cases are caused by contamination with disease-inducing viruses. The object was therefore to make available, by inactivation and/or elimination of viruses of this type, highly purified plasma preparations and preparations of blood clotting factors which can be used in patients without danger of a virus infection. A number of processes have already been proposed for this.

Thus, European Patent 0 124 506 discloses a process for the inactivation of proliferative pathogens in preparations which contain plasma enzymes, clotting factors, immunoglobulins or other proteins present in the blood, in which the preparation is brought to a salt concentration of more than 0.5 molar by addition of ammonium sulfate and heat-treated, whereupon the salt is removed from the preparation. In this process, ammonium sulfate is added to a preparation having a protein content of up to 30% until a 2- to 4-molar concentration is reached. A heat treatment is then carried out during a period of up to 100 hours and at a temperature of 40 to 121° C. Of course, in a process of this type attention must be paid to the fact that in the salt and heat treatment used not only the viruses are inactivated and/or eliminated, but that in this case also the biological activity of the plasma proteins contained in the preparation is retained to as high an extent as possible. A need therefore furthermore exists for processes for the inactivation and/or elimination of viruses from a plasma protein solution, which not only fully exclude the transmission of virus infections by plasma preparations of this type, but moreover are so gentle that the biological activities of the plasma proteins, in particular also of the blood clotting factors, are not adversely affected.

It has now been found that these requirements are fulfilled in an excellent manner by a process for the inactivation and/or elimination of coated and/or noncoated viruses from a plasma protein solution if a plasma protein solution is subjected to incubation at room temperature and alkaline pHs at an ammonium salt concentration of 13 to 22% by weight (=25 to 39% ammonium sulfate saturation), pasteurized at approximately 60° C for several hours after separation of the precipitates and the removal of the ammonium salt down to a residual content of less than 0.5 mol/l and then processed to give a therapeutically employable plasma protein preparation.

Plasma proteins within the meaning of the invention are not only the intact, active proteins themselves, but also their precursors. The plasma proteins can be obtained from plasma or other body fluids.

For this process, a plasma protein solution previously purified by affinity chromatography is preferably employed and the process is carried out at a pH of between 8 and 11. The virus reduction takes place either by elimination, e.g. in the case of the canine parvovirus (CPV), where a temperature of 25±1° C. is very particularly preferred, or by a combination of elimination and inactivation, e.g. in the case of the bovine virus diarrhea virus (BVDV) or in the case of HIV.

A further improvement in the process according to the invention can be achieved by adding ammonium salt again after the incubation with an ammonium salt concentration of 13 to 22% by weight (=25 to 39% ammonium sulfate saturation) and removal and precipitation of the impurities by centrifugation or filtration, and increasing the concentration to 24 to 27% by weight (=44.4 to 50% ammonium sulfate saturation). In this second precipitation, the plasma protein is precipitated in pure form and then pasteurized at approximately 60° C. for several hours after removal of the ammonium salt down to a residual content of less than 0.5 mol/l. The precipitate can then be processed to give a therapeutically employable plasma protein preparation.

2 to 4 hours should be used both for the first and the second incubation. The ammonium salt employed is preferably ammonium sulfate.

In order to obtain a residual activity of the plasma proteins which is as high as possible, it is recommended to carry out the pasteurization in the presence of stabilizers. A suitable stabilizer has proved to be a mixture of sucrose (1000 g/l) with glycine (150 g/l). A high residual activity of the plasma proteins can also be obtained in the presence of sucrose and potassium acetate as stabilizers. In general, the process according to the invention is carried out with plasma proteins obtained from blood and affords a residual activity of up to 95% (based on antithrombin III). However, it can be employed as well also for biotechnologically prepared, recombinant or transgenic plasma proteins which are obtained from single-celled organisms or especially also from transgenic animals.

The maintenance of alkaline pHs is also of particular importance for the process according to the invention. If the pH is increased under otherwise identical conditions, an increase in the virus inactivation can be observed with increasing pH in the protein purification which is achieved by the precipitation reaction. The increased virus reduction can be found both for coated and for noncoated viruses and is attributed to the combination of the effects of ammonium salt and alkaline pH.

It is thus characteristic of the process according to the invention that it contains two virus-reducing process steps, namely pasteurization in aqueous solution (10 hours, 60° C.) and ammonium sulfate precipitation. Both virus inactivation steps have high reduction factors in virus reduction. The effect of both steps even on noncoated viruses is of particular importance.

The process according to the invention can be described in the following way as exemplified by antithrombin III (AT III):

Human antithrombin III is isolated from donor blood which, after cryoprecipitation by centrifugation, is separated into corpuscular and plasmatic constituents. The 8% ethanol supernatant obtained on Cohn fractionation is prepurified using a heparin Fractogel chromatography column. In this process, AT III is enriched on the column. The heparin attached to the column binds both AT III and some other plasma proteins. The majority of the loosely bound plasma proteins are washed off using a buffer solution having a low NaCl concentration, whereas AT III is subsequently eluted using a buffer solution consisting of 2 M NaCl, 50 mM $NaH_2PO_4$ and a pH of 7.5. The high purity of AT III which is already achieved by this specific affinity chromatography is further improved by the elimination of contaminating proteins by fractional ammonium sulfate precipitation. A concentration of 31.3% ammonium sulfate saturation is then established in the eluate by addition of solid ammonium sulfate. During incubation at room temperature (25° C.±1) for three hours, a precipitate is formed which is separated off by centrifugation or filtration and discarded. Excessively vigorous stirring is to be avoided during the incubation, because otherwise the precipitate becomes too fine and blocks the filter. A pH of 9.0 is maintained during the incubation. The concentration of ammonium sulfate is then reduced by dialysis down to a residual content of less than 0.5 mol/l and sucrose (1000 g/l) and glycine (150 g/l) are added as stabilizers. The aqueous, stabilized AT III solution is then pasteurized at 60° C. for 10 hours.

The high purity of the final product was confirmed by zone electrophoresis and polyacrylamide gel electrophoresis.

For the investigation of virus depletion, viruses are added before the ammonium sulfate treatment (0.05 part by volume). In this case, the following values for virus depletion were found:

TABLE I

| Virus | Virus reduction factor ($\log_{10}$) |
|---|---|
| HIV | $\geq 7.8$ |
| HAV (hepatitis A virus) | $\geq 6.1$ |
| PRV (pseudorabies virus) | $\geq 7.7$ |
| BVDV (bovine virus diarrhea virus) | $\geq 7.1$ |
| CPV (canine parvovirus) | $\geq 8.1$ |

A second ammonium sulfate precipitation, in which the concentration is adjusted to a final concentration of 45.9% ammonium sulfate saturation by addition of solid ammonium sulfate, can preferably follow the first ammonium sulfate precipitation. After a precipitation time of 3 hours at room temperature, the precipitated AT III is separated off. The precipitate thus obtained is then adjusted to a buffer of 0.8% (w/v) NaCl and 0.8% (w/v) ammonium sulfate by dissolution and dialysis.

For the investigation of virus inactivation by pasteurization, infectious viruses were added to the product immediately before pasteurization and the sample was then subjected to heat treatment at 60° C. It was observed that all viruses investigated (with the exception of CPV) were completely inactivated after a heat treatment of less than 6 hours.

The guidelines for the European Union issued by the Committee for Proprietary Medicinal Products (CPMP) require the stepwise investigation of the virus elimination/inactivation through the process of preparation of a human plasma protein. According to these guidelines, at least three species of virus should be used for investigations of this type, namely HIV as the relevant risk virus, a further coated virus and a noncoated virus. The above table shows that excellent reduction factors for very different types of virus were achieved using the process according to the invention.

For the investigation of virus safety, the AT III preparations produced by the process according to the invention were subjected to a clinical study. 13 healthy male subjects who had previously received neither blood transfusions nor blood derivatives and in whom no histories of a liver disorder existed were admitted into this study. 7 subjects were inoculated against hepatitis B and therefore possessed protective antibodies of the type anti-HBs. The other 6 participants had a negative result to hepatitis B serum markers. Safety against hepatitis B could therefore only be monitored in these 6 subjects, whereas all 13 subjects were assessable with respect to hepatitic C and HIV infections. Each participant in this study received two different batches of the pasteurized AT III concentrate on a randomized basis and was treated with two different doses; i.e. 8 received fixed doses of 1000 units, whereas the other 5 in each case received 50 units per kg of body weight. On average, the amount of AT III administered to the latter group was approximately 3600 units per person. All subjects were examined for transaminases during the first six months at two-week intervals and then every four weeks. The transmission of hepatitis non-A non-B virus was regarded as confirmed if the serum transaminase level in two successive examinations exceeded 2.5 times the upper normal threshold value and if all other hepatitis viruses were excluded. Afterwards, the serum samples of each subject were also investigated for anti-HCV and anti-HIV-2 antibodies. Hepatitis B serum markers (HBsAg, anti-HBc, anti-HBs) and anti-HIV 1 were tested every two months.

After an observation time of 12 months, increased serum transaminase activities were found in none of the 13 subjects, and none had a positive result to anti-HIV or anti-HCV. Moreover, none of the 6 subjects who were not inoculated with hepatitis B vaccine developed positive HIV markers.

On the basis of this clinical study, which was carried out according to the recommendations of the International Committee of Thrombosis and Hemostasis (ICTH), and on the basis of the retrospective analysis of patients who were treated with the AT III concentrate produced by the process according to the invention, it can be concluded that the AT III preparation produced by the process according to the invention is not affected by the risk of HBV, HCV or HIV contamination.

The experimental data obtained using the AT III preparation investigated show that the resulting, pasteurized AT III preparation is purified almost to homogeneity and that this product achieves a high safety margin, because viruses are effectively eliminated and inactivated in various phases of the production process. By means of combination of precipitation reactions and pasteurization, a virus reduction is achieved in this case which guarantees an extremely high safety standard of the plasma protein preparations thus produced.

At the same time, it is to be emphasized that the process according to the invention is particularly gentle owing to the removal of the ammonium salt from the protein solution purified by the precipitation reaction to a residual content of <0.5 mol/l and guarantees that particularly high residual activities of the plasma proteins are retained in the subsequent pasteurization.

In the case of the plasma proteins mentioned in Table II, the process according to the invention led to the high residual activities mentioned therein.

TABLE II

| Active compound | Precipitation range in % ammonium sulfate saturation | Precipitation range in % (w/v) ammonium sulfate | Optimal precipitation concentration in % ammonium sulfate saturation | Optimal precipitation concentration in % (w/v) ammonium sulfate | Residual activity (after precipitation) |
|---|---|---|---|---|---|
| Antithrombin III | 24.1–38.9% | 13–21% | 31.5% | 17% | >90% |
| C1 inactivator | 29.6–38.9% | 16–21% | 35.2% | 19% | >90% |
| Thrombin or prothrombin | 29.6–38.9% | 16–21% | 35.2% | 19% | 70–80% |
| Factor V, factor VII, factor X | 29.6–38.9% | 16–21% | 35.2% | 19% | 70–80% |
| Factor IX | 29.6–44.4% | 16–24% | 40.7% | 22% | 70–80% |
| API | 20.4–35.2% | 11–19% | 24.1% | 13% | 70–80% |

According to Table II, the precipitation conditions of antithrombin III also apply to the active compounds C1 inactivator, thrombin and prothrombin, factor V, factor VII and factor X. For factor IX, the optimal precipitation concentration is 22% (w/v) ammonium sulfate or 40.7% ammonium sulfate saturation.

For ($\alpha_1$-antitrypsin, the optimal precipitation concentration is rather 13% (w/v) ammonium sulfate or 24.1% ammonium sulfate saturation.

For the production of a therapeutically employable plasma protein preparation, the protein precipitate obtained in the process according to the invention is introduced into an injection vial as dry matter in the form of a plasma fraction enriched with the protein precipitate. The excipients employed are aminoacetic acid, sodium chloride and sodium citrate. An ampoule containing 10 ml of water for injections, pyrogen-free, is added to the injection vial.

What is claimed is:

1. A process for the inactivation and/or elimination of coated and/or noncoated viruses from a plasma protein solution comprising:
   a) incubating at room temperature and at an alkaline pH the plasma protein solution containing an ammonium salt concentration ranging from 13 to 22% by weight;
   b) separating precipitates from the plasma protein solution;
   c) removing from the plasma protein solution the ammonium salt to provide a residual content of less than 0.5 mol/l; and
   d) pasteurizing the plasma protein solution at approximately 60° C. for several hours.

2. The process as claimed in claim 1, further comprising in place of step c) the following steps:
   c1) precipitating the plasma protein solution by increasing the ammonium salt concentration in the plasma protein solution to an amount ranging from 24 to 27% by weight;
   c2) separating the precipitated plasma protein from the remaining solution; and
   c3) dissolving the precipitated plasma protein to provide a residual ammonium salt of less than 0.5 mol/l.

3. The process as claimed in claim 1, wherein the plasma protein solution employed is a plasma protein solution which is prepurified by affinity chromatography.

4. The process as claimed in claim 1, wherein the process is carried out at a pH ranging from 8 to 11.

5. The process as claimed in claim 1, wherein step a) is carried out for 2 to 4 hours.

6. The process as claimed in claim 1, wherein the ammonium salt employed is ammonium sulfate.

7. The process as claimed in claim 1, wherein the pasteurization is carried out in the presence of sucrose and glycine or in the presence of sucrose and potassium acetate as stabilizers.

8. The process as claimed in claim 1, wherein the process is carried out using natural or biotechnologically produced plasma proteins.

9. A plasma protein solution obtained by:
   a) incubating at room temperature and at an alkaline pH the plasma protein solution containing an ammonium salt concentration ranging from 13 to 22% by weight;
   b) separating precipitates from the plasma protein solution;
   c) removing from the plasma protein solution the ammonium salt to provide a residual content of less than 0.5 mol/l;
   d) pasteurizing the plasma protein solution at approximately 60° C. for several hours; and
   e) processing the plasma protein solution to give a therapeutically employable plasma protein solution.

* * * * *